United States Patent [19]
Domenico

[11] Patent Number: 5,928,671
[45] Date of Patent: *Jul. 27, 1999

[54] METHOD AND COMPOSITION FOR INHIBITING BACTERIA

[75] Inventor: Philip Domenico, Elmhurst, N.Y.

[73] Assignee: Winthrop University Hospital, Mineola, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/883,584

[22] Filed: Jun. 26, 1997

Related U.S. Application Data

[63] Continuation of application No. 08/428,464, Apr. 25, 1995, abandoned.

[51] Int. Cl.⁶ .................. A61K 31/095; A61K 33/24
[52] U.S. Cl. ............................. 424/653; 514/706
[58] Field of Search ........................... 424/653; 514/706

[56] References Cited

U.S. PATENT DOCUMENTS

| | | | |
|---|---|---|---|
| 2,809,971 | 10/1957 | Bernstein et al. | 260/270 |
| 3,583,999 | 6/1971 | Damico | 260/294.8 |
| 3,753,990 | 8/1973 | Curry | 260/270 |
| 3,773,770 | 11/1973 | Damico | 260/290 |
| 3,833,565 | 9/1974 | Curry | 260/270 |
| 3,852,441 | 12/1974 | Kooistra, Jr. | 424/245 |
| 3,890,242 | 6/1975 | Curry | 252/107 |
| 4,374,825 | 2/1983 | Bolich, Jr. et al. | 424/70 |
| 4,524,110 | 6/1985 | Heeres et al. | 428/537.1 |
| 4,963,344 | 10/1990 | Gries et al. | 424/9 |
| 5,104,645 | 4/1992 | Cardin et al. | 424/70 |
| 5,541,233 | 7/1996 | Roenigk | 521/54 |
| 5,593,670 | 1/1997 | Trinh et al. | 424/76.1 |
| 5,596,102 | 1/1997 | Austin | 548/101 |
| 5,605,681 | 2/1997 | Trandai et al. | 424/65 |
| 5,624,666 | 4/1997 | Coffindaffer et al. | 424/70.21 |
| 5,643,971 | 7/1997 | Roenigk | 523/122 |

FOREIGN PATENT DOCUMENTS 9412034  6/1994  WIPO .

OTHER PUBLICATIONS

W. Beil et al., Pharmacology 50:333–337 (1995).
D.W. Bierer, Rev. Infect. Dis. 12(1):S3–S8 (1990).
D. Chaleil et al., J. Inorg. Biochem. 15:213–221 (1981).
N.A. Cornick et al., Rev. Infec. Dis. 12(1):S9–S10 (1990).
J.S. Dixon, Scand. J. Gastroenterol. 30(212):48–62 (1995).
P. Domenico et al., J. Antimicro. Chemo. 28:801–810 (1991).
P. Domenico et al., Infection 20(2):18/66–23/71 (1992).
P. Domenico et al., Eur. J. Clin. Microbiol. Infec. Dis. 11:170–175 (1992).
P. Domenico, "Comparative Antibacterial Properties of Bismuth–Dimercaprol and Chlorhexidine," 95th Gen'l. Meeting Amer. Soc. Microbiol., Washington, D.C. (May 1995).
P. Domenico et al., "Bismuth–Dimercaprol Activity Against Multiply Resistant Gram–Positive Bacteria," Clin. Res. Meeting, Abstract (May 1995).
P. Domenico et al., In vitro Antifungal Activities of BisBAL and BisME, Two Thiol–Chelated Bismuth Compounds, 36th ICAAC, Abstract F188 (Sep. 1996).
P. Domenico et al., "Efficacy/Toxicity of Bismuth–Dimercaprol in a Burn Wound Sepsis Model," 96th ASM General Meeting, Abstract A10 (May 1996).
P. Domenico et al., "Antimicrobial Activity of the Bismuth–Thiol Chelates, BisBAL and BisME," Clin. Res. 44:332A, Abstract (1996).
P. Domenico et al., Annals of N.Y. Acad. Sci. 797:269–270 (1996).
P. Domenico et al., Antimicrob. Agents and Chemo. 38(6):1031–1040 (1997).
P. Domenico et al., Antimicrob. Agents and Chemo. 41(8):1697–1703 (1997).
P. Domenico et al., "Potentiation of Bismuth Antibacterial Activity by Thiol Chelators," 97th ASM Gen'l. Meeting, Florida, Official Abstract Form & Abstract A–43 (May 1997).
B.E. Douglas et al., Concepts and Models of Inorganic Chem., 3rd Ed. pp. 463–465 1994).
H.L. DuPont et al., New Eng. J. Med. 328:1821–1827 (1993).
D. Figueroa–Quintanilla et al., New Eng. J. Med. 328(23):1653–1658 (1993).
S.L. Gorbach et al., Reviews of Infec. Dis. 12(1):S21–S23 (1990).
Gould et al., "Activity of the Novel Compounds BisBAL and BisME Against *Burkholderia cepacia,*" 36th ICAAC, Louisiana, Abstract F246 (1996).

(List continued on next page.)

Primary Examiner—Phyllis Spivack
Attorney, Agent, or Firm—Ostrolenk, Faber, Gerb & Soffen, LLP

[57] ABSTRACT

A composition comprising a trivalent bismuth salt, particularly bismuth nitrate, and dimercaprol is described. Methods for using the composition as a bacteriocidal and bacteriostatic agent and as a disinfectant and preservative are also provided.

18 Claims, 1 Drawing Sheet

OTHER PUBLICATIONS

D.Y. Graham et al., Ann. Intern. Med. 115:266–269 (1991).
D.Y. Graham et al., Gastroenterol. 102:493–496 (1992).
W. Hespe et al., Gastroenterol. 104(4):1242–1243 (1993).
R. Husseini et al., Microbios 29(116):109–125 (1980).
R. Iffland, "Bismuth" in *Metals in Clinical and Analytical Chemistry*, Marcel Dekker, Inc. Chap. 21, pp. 269–281 (1994).
T. Klapötke, Biol. Metals 1:69–76 (1988).
M.D. Manhart, Reviews of Infec. Dis. 12(1):S11–S15 (1990).
B.J. Marshall, Reviews of Infec. Dis. 12(1):S87–S93 (1990).
Molina et al., Acta. Neurol. Scand. 79:200–203 (1989).
Molina et al., Med. Clínicas 93(1):20–22 (1989).
G.L. Newton et al., Methods of Enzymology, vol. 251, pp. 148–166, Academic Press (1995).
P–M. Roy et al., The Lancet 344:1708 (1994).
K.W. Shea et al., "Vancomycin Resistant Enterococci (VRE) Colonization in an Outpatient Hemodialysis (HD) Unit," 6th Ann. Mtg. of the Soc. for Healthcare Epidemiology of America, Official Abstract Form (Apr. 1996).
A. Slikkerveer et al., Med. Toxicol. Adverse Drug. Exp. 4(5):303–323 (1989).
A.P.R. Wilson, The Lancet 344:1313–1314 (1994).
"The Pharmacological Basis of Therapeutics, Heavy Metal Antagonists, Halogens and Halogen–Containing Compounds," 7th Ed., Goodman & Gilman, pp. 963–964 and 1621–1622 (1985).

Meta–Analysis of the Efficacy of Antibiotic Therapy in Eradicating Helicobacter pylori, Naoki Chiba, M.D.; Babu V. Rao, M.D.; Johan W. Rademaker, M.D.; and Richard H. Hunt, M.D.; The American Journal of Gastroenterology, vol. 87, No. 12, 1992, pp. 1716–1727.

Studies on the Mechanism of Action of Colloidal Bismuth Subcitrate (1. Interaction with Sulfhydryls); W. Beil, S. Bierbaum, K.–F. Sewing; Pharmacology, 1993; 47:135–40.

Studies on the Mechanism of Action of Colloidal Bismuth Subcitrate (2. Interaction with Pepsin); W. Beil, S. Bierbaum, K.–F. Sewing; Pharmacology, 1993; 47:141–144.

Colloidal Bismuth Subcitrate: A Review of its Pharmacodynamic and Pharmacokinetic Properties, and Its Therapeutic Use in Peptic Ulcer Disease; Antona J. Wagstaff, Paul Benfield and Jon P. Monk; Drugs 36: 132–157 (1988).

P. Domenico & B.A. Cunha, "Synergistic Inhibitory Effects of Bismuth and Demercaprol Against Gram–Negative Bacteria", Apr. 26, 1994, 6th International Congress for Infectious Diseases, Prague, Czech Republic.

P. Domenico & B.A. Cunha, "Mechanism of Bismuth–Dimercaprol Antimicrobial Synergy", Oct., 1994, 34th ICAAC, Orlando, Florida.

METHOD AND COMPOSITION FOR INHIBITING BACTERIA

This is a continuing application of apprication Ser. No. 08/428,464 filed on Apr. 25, 1995 abandoned.

BACKGROUND OF THE INVENTION

1. Field of the Invention

The present invention relates to a composition and a method for the amelioration and inhibition of bacterial infections, and more particularly, to a composition of a trivalent bismuth salt and dimercaprol. Bacteriocidal and bacteriostatic properties are demonstrated.

2. Description of the Prior Art

Infectious diseases of the digestive tract constitute a major health problem throughout the world. Infectious diarrheal disease is one of the leading causes of morbidity and mortality in developing countries. In developed countries, diarrhea and colitis are frequent symptoms during antibiotic therapy. Food contamination with Salmonella, Shigella, Campylobacter, or *E. coli* poses a major health problem. Diarrhea is the most frequent discomfort among travelers. Even ulcers are now considered an infectious disease.

The finding in 1983 that *Helicobacter pylori* was the probable cause of ulcers has precipitated intense activity in developing therapies to eradicate this organism from the gastro-intestinal (GI) tract. Effective therapies have emerged, involving combinations of antibiotics, $H_2$-inhibitors and bismuth compounds. These therapies demonstrate an absolute requirement for bismuth to achieve a long-term cure with little probability of reinfection. At present, the preferred form to administer bismuth is as the subcitrate (colloidal bismuth subcitrate or CBS) or as the subsalicylate (BSS, a.k.a. Pepto-Bismol®).

The mechanisms by which CBS or BSS help to eradicate *H. pylori* are not fully understood and are currently under investigation. For a review of the properties of CBS, see Wagstaff, et al., Drugs 36:132–157 (1988). Apparently no single mechanism of bismuth activity can account for all of the antiulcer effects suggested in the literature. Indeed a number of therapeutic activities may be involved. Experiments recently performed by Beil et. al., Pharmacology; 47:135–140 (1993) investigated the interactions between colloidal bismuth subcitrate (CBS) and sulfhydryls and their results indicated that DTT did not enhance the antibacterial activity of CBS.

Bismuth compounds are also used in numerous other medical applications. For example, they are used orally as an anti-diarrheal agent, for an upset stomach, nausea, vomiting, and as an internal deodorant, and as skin antiseptics. Bismuth compounds are also used prophylactically for Traveler's diarrhea, and as an iodoform paraffin paste, they are used to limit infection of surgical wounds. In general, bismuth has antibacterial properties with proven medical usefulness.

Bismuth also has selective effects on expression of virulence factors in bacteria. Concentrations below that which inhibited bacterial growth nevertheless repressed the expression of capsular polysaccharide (CPS) from *K. pneumoniae* and other members of its family Enterobacteriaciae. It also represses the expression of certain pili involved in adherence. The antibacterial potency of bismuth is especially strong under low iron conditions. Increasing iron negates the inhibitory effects of bismuth on bacteria.

Compared to other antimicrobial agents, the potency of bismuth compounds is relatively low, especially when iron is present. In addition, one of the major problems with using bismuth is its insolubility in aqueous solutions.

SUMMARY OF THE INVENTION

It is thus an object of the present invention to provide a composition and a method for inhibiting bacterial growth and for preventing bacterial infection. In particular, a composition which includes a trivalent bismuth salt such as BSS, CBS or $Bi(NO_3)_3$ and dimercaprol [2,3-dimercaptopropanol, British anti-lewisite (BAL)] is provided. When combined, a synergy occurs that enhances the inhibitory action of $Bi^{3+}$ against bacteria from 100 to 1000-fold. The concentration of both agents can be reduced to nontoxic levels and the combination still possesses powerful bacteriostatic and bactericidal activities against nosocomial pathogens. The composition has broad spectrum bacteriostatic and bacteriocidal effects and therefore is useful as an antibacterial, antiseptic and antimicrobial agent for preventing infection and for disinfecting and cleaning surfaces. It can also be used as a preservative and for killing biofilm organisms and preventing the formation of a biofilm. In particular, the composition of the present invention is useful for treating bacterial infections of the gastro-intestinal (GI) tract. Other agents such as antioxidants, carriers, detergents, antibiotics, preservatives can be used in combination with the composition.

Other features and advantages of the present invention will become apparent from the following description of the invention which refers to the accompanying drawing.

DETAILED DESCRIPTION OF THE INVENTION

Figure 1:
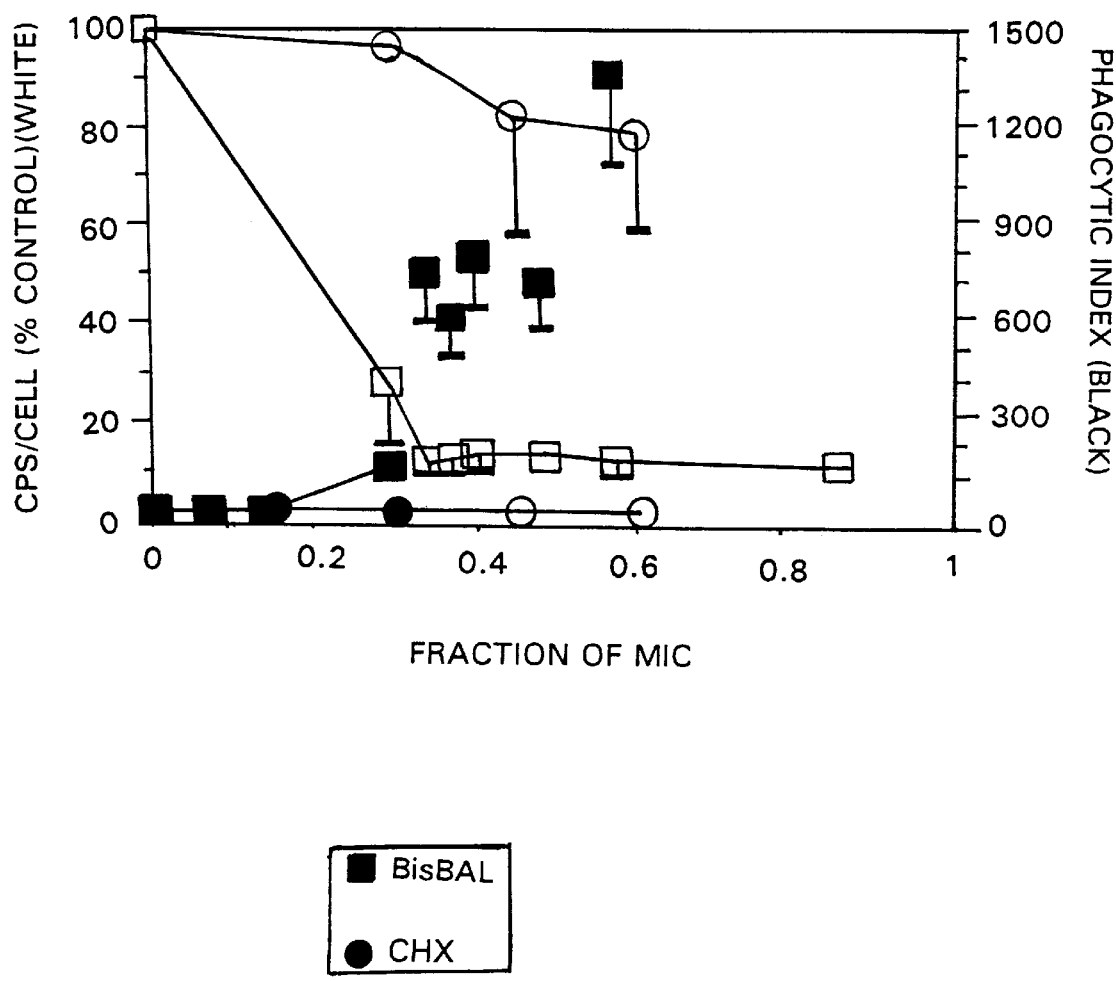
FIG. 1 is a graph showing the comparative effects of BisBAL and chlorhexidine on capsule and slime expression by bacteria.

A novel composition of a trivalent bismuth salt and BAL (BisBAL) has been prepared which shows significant broad spectrum bacteriocidal and bacteriostatic properties. The BisBAL composition can be prepared by any standard method. In a preferred embodiment, for 50 mM $Bi^{3+}$, add 24.3 mg $Bi(NO_3)_3$ to 960 µL propylene glycol and 40 µl 10 N NaOH. For BAL (Sigma; 10M solution of dimercaprol; 124 g/mol) serial 10-fold dilutions are prepared in water. Stock solutions of BisBAL at 50 mM/110 mM are made by dissolving 243 mg in 9.7 ml $H_2O$, adding 110 µl 10 M BAL, and adjusting the pH to between 8 and 10 with 180–200 µl 10 N NaOH. The effect of subjecting BisBAL stock solutions to extreme temperatures on antibacterial activity were tested by heating to boiling and by autoclaving. BisBAL was found to be heat labile and destroyed by autoclaving. Stability of various BisBAL preparations kept at room temperature and at 4° C. for long periods was tested periodically. BisBAL was found to be a fairly stable compound. BisBAL activity is stable for at least one month if kept at 4° C., but at room temperature (RT) a 500/600 µM BisBAL solution will lose 50% of its activity in two weeks. A 500/150 µM BisBAL solution loses 50% of its activity at RT in a few days. If desired, an alkaline compound, such as NaOH, can be added to adjust the pH and solubilize the mixture.

It has been found that the ideal molar ratio of bismuth to BAL is in a ratio range of approximately 1:2 to 3:1. At a ratio of 3:1, the composition is particularly active against microbes. However, the highest solubility in water and longest shelf life can obtained when the molar ratio of bismuth to BAL is 1:2. Differing ratios can be used depending on the desired characteristics of the composition.

While it is not possible to bring 50 μM of $Bi^{3+}$ into solution in $H_2O$, 500 mM $Bi^{3+}$ goes into solution with 1.2 M BAL present at pH 9–10. Furthermore since BAL is lipophilic, BisBal is soluble in acetone, ethanol, isopropanol, acetonitrile, DMSO, and even 1-butanol, but not in chloroform, octanol, ethyl acetate, or isoamylalcohol.

Based on gel filtration analysis, BisBal is thought to be a polycation. It was found that the majority of the yellow pigment of BisBAL preparations eluted from a BioGel P2 column at an apparent molecular weight of 1000 daltons, which is consistent with the structure of a polycation. BisBAL is highly positively charged on one end which adds to its water solubility. On the other end, it is lipophilic and thus soluble in nonpolar solvents.

The affinity of BAL for $Bi^{3+}$ is great since when the pH of concentrated BisBAL solutions drops below the alkaline range, a yellow precipitate forms. $Bi^{3+}$ alone forms a white precipitate. After sedimenting the precipitate, removing the supernatant and adding fresh alkaline buffer, the precipitate will redissolve, indicating that the precipitate is not $Bi^{3+}$ alone but rather intact BisBAL. This suggests that BisBAL may precipitate in the acidic stomach, but will redissolve in the small intestine.

It has been found that the optimum $Bi^{3+}$ doses are in the range of 0.01 mg/kg to 357 mg/kg per day with the oral and topical dose not exceeding 500 mg/kg of BAL and an injected dose not exceeded 50 mg/kg of BAL. This is consistent with the extended regimen in humans for Pepto-Bismol®, in which 30 ml (525 mg BSS) are administered four times a day (2.1 g/day) for 3 weeks. Maximal intake of BSS in humans is 4.2 g/day. This is the equivalent of 18 mg/day of $Bi^{3+}$ in a 30 g mouse, or 600 mg/kg/day, or 300 mg/kg bid. The maximum oral dose of $Bi^{3+}$ in BSS for humans is similar to the highest safe dose of BisBAL for mice. Thus, the maximum $Bi^{3+}$ concentration already established for other therapeutic $Bi^{3+}$ compounds need not be altered for BisBAL therapy. Surprisingly, BisBAL is less toxic than existing $Bi^{3+}$ compounds, even though it is over 1000-fold more potent against bacteria. It has been found that BAL is the limiting factor, since at high doses BAL is toxic, with rapid death accompanied by severe tremors.

When injected intraperitoneally into mice, BisBAL ($LD_{50}=140\pm40$ mg$Bi^{3+}$/kg) was considerably less toxic than Bi($NO_3$)$_3$ ($LD_{50}=52\pm13$ mg$Bi^{3+}$/kg) or Bi-cysteine ($LD_{50}=49\pm12$ mg$Bi^{3+}$/kg), based on two separate trials. Mice can tolerate 60 mg $Bi^{3+}$ kg in the form of BisBAL intraperitoneally without signs of morbidity or mortality for at least 5 days. Therefore $Bi^{3+}$/kg is less toxic as the BisBAL chelate than in other compounds, especially when given intraperitoneally.

Experiments of the toxicity of BisBAL were performed in 35 g Swiss-Webster female mice. The BisBAL was administered orally and intraperitoneally. As shown in Table I, the mice tolerated 12.5 mg of $Bi^{3+}$ orally (357 mg/kg; 50 equivalent human doses) with fairly high doses of BAL. Combined with $Bi^{3+}$, BAL doses of 500 mg/kg were innocuous, while 1 g/kg killed all of the mice within a few hours. When given alone, BAL at 500 mg/kg killed all of the mice within an hour, and BAL at 250 mg/kg killed one of five mice.

The oral $LD_{50}$ for BAL alone is calculated to be 333 mg/kg. The intramuscular $LD_{50}$ for BAL alone in rats is 86.7 mg/kg (Merck Manual). The intraperitoneal $LD_{50}$ for BAL in mice is 60 mg/kg. The oral $LD_{50}$ for mice is over 5-fold higher, presumably due to limited absorption of BAL from the gut. The oral $LD_{50}$ for BAL in BisBAL is even higher at 556 mg/kg. Evidently, $Bi^{3+}$ lessens oral toxicity of BAL. Thus, BAL is the toxic moiety in BisBAL oral preparations, but is not as toxic orally when combined with $Bi^{3+}$. Indeed, BAL given orally in BisBAL is nearly 10 times less toxic than is BAL given intraperitoneally.

The threshold toxic intramuscular dose for BAL in humans is less than 5 mg/kg (Sulzberger, 1946), which is one-hundredth the BAL that was tolerated orally as BisBAL. These data suggest that BAL toxicity should not be problematic during BisBAL therapy since the minimal inhibitory concentration (MIC) for BAL in BisBAL is 100–500 μg/kg.

TABLE I

| Agent | Oral $LD_{50}$ (mg/kg) | IP $LD_{50}$ (mg/kg) |
|---|---|---|
| Bi($NO_3$)$_3$ | >357 | 53 ± 13 |
| BAL | 333 ± 60 | 60 ± 10 |
| BisBAL | 357/556 ± 25 | 142 ± 54/234 ± 91 |
| Bi-cysteine | 156 ± 20 | 49 ± 12 |

In additional experiments, burned mice were challenged with K. pneumoniae to investigate the topical toxicity of BisBAL. When BisBAL at 376/621 mg/kg was applied topically or subeschar mortality was hastened by 2–3 days. However, 38/62 mg/kg did not hasten mortality when applied topically and 3.8/6.2 mg/kg did not affect mortality when applied either topically or subeschar. The lethality of BisBAL in a burn wound sepsis model paralleled that seen in oral models. The data indicates that the threshold for BAL toxicity orally or topically, in the form of BisBAL is greater than 500 mg/kg, while the systemic toxicity threshold is greater than 50 mg/kg.

As a disinfectant, or for use on inanimate surfaces, BisBAL concentrations can exceed the limits set forth above. In particular, concentrations up to and exceeding 500 mM $Bi^{3+}$ and 1M BAL can be used for disinfectant purposes. Further, concentrations as low or lower than 50 μM $Bi^{3+}$ and 100 μM BAL can be used for antiseptics or preservatives.

Another consideration is the toxicity of BisBAL for mammalian cells. BisBAL was not notably cytotoxic or pro-inflammatory based on animal studies and other informal observations. There was no evidence of blood or mucus in the stools of treated animals, nor any signs of irritability from massive doses of BisBAL. Accidental contact on hands with small amounts of BAL can be quite irritating, whereas BisBAL is not irritating to the skin even at 100-fold the BAL concentration. BAL alone is very toxic and extremely irritating to gastric mucosa when applied as 5% solutions (Cattell, 1942). Preliminary results further showed that BisBAL was not cytotoxic to neutrophils, even at 100x bacteriostatic concentrations.

Any trivalent bismuth salt can be used in the preparation of the composition, including BSS, CBS and bismuth nitrate Bi($NO_3$)$_3$. It is preferable, however, to use bismuth nitrate. It is also possible to use dithiothreitol (DTT) or β-mercaptoethanol (βME) instead of BAL.

The following experiments show that the Bis-BAL composition can inhibit the growth of a broad spectrum of bacteria, including gram positive and gram negative bacteria, as well as aerobic and anaerobic bacteria.

EXAMPLE 1

Bacteria and Culture Conditions

Nosocomial pathogens were employed to determine the range of BisBAL antimicrobial activity. The following bacteria were cultured in a standard broth medium, e.g., Mueller-Hinton II, overnight: *Klebsiella pneumonia* O1:K2 strain 52145, Non O1 *Vibrio cholerae* strain NRT36S, *Salmonella enteritidis* strain ATCC 14028, *Shigella flexneri* ATCC 12022, *Yersinia enterocolitica* ATCC 27729, enterohemorrhagic *Escherichia coli* 0157:H7 (ATCC 35150), and enterotoxigenic *Escherichia coli* ATCC 43896. Anaerobes included *Clostridium perfringens* ATCC 13124 and *Bacteroides fragilis* ATCC 23745. Ten *Pseudomonas aeruginosa* strains resistant to aminoglycoside antibiotics were obtained from the Schering-Plough collection. Several clinical isolates of Providencia, Serratia, and Xanthomonas were tested; Proteus strains included *P. vulgaris* O:19, *P. vulgaris* ATCC 49990, *P. mirabilis* ATCC 49995, *P. mirabilis* ATCC 51286, and *P. mirabilis* ATCC 49565, *Pseudomonas cepacia* Isolates of *H. pylori,* methicillin-resistant *S. aureus* (MRSA) and vanomycin-resistant enterococci (VRE) were also used. Reference strains of *Staphylococcus aureus* (ATCC 25923), *Excherichia coli* (ATCC 25922), and *Pseudomonas aeruginosa* PAO1 were provided for comparison. Pyoverdene mutants of *P. aeruginosa,* PAO6609 and K394 were employed. The following iron receptor mutants were used: *E. coli* H1443 (wt), *E. coli* H854 (fiu), *E. coli* C1087 (cir), *E. coli* C1072 (tonB), *E. coli* AB1515-and *E. coli* AB1515-1F ($Fe^{2+}$ transport deficient). Multiple antibiotic resistance (mar) and sox mutants of *E. coli* were utilized and included strains MC4100 (wt), MC4100/p9 (Mar), MC4100 Tn9 $\Delta$1738 and MC4100 Tn10kan soxR201. These strains were maintained by subculture on agar medium containing ampicillin (50 $\mu$g/ml), kanamycin (20 $\mu$g/ml), or chloramphenicol (10 $\mu$g/ml) as needed. *Vibrio cholerae* strains included 395, 569, El tor Ogawa N16961, El tor Inaba P27459, 1837, 168019, and MO-10. Strains 1837, 168019 and MO-10 are known to have capsules. Bacteria were subcultured weekly on Blood or Nutrient agar plates.

A Mueller Hinton II broth (BBL Systems, USA) was the culture medium used in most susceptibility studies. A chemically-defined medium with excess glucose and limiting nitrogen (DW) was used to promote capsule production in *K. pneumoniae* cultures (Domenico, 1991). MacFarland standard suspensions (0.5) were prepared from mid-log phase starter cultures and further diluted 1:100 into test medium. Bacteria were placed in customized research cuvettes with chemotherapeutic agent, and loaded in the Advantage System (Abbott Laboratories, USA). Cultures were rocked slowly at 34.5° C. and monitored repeatedly at $A_{670}$ nm. Inhibition was assessed by recording lag times before initiation of culture growth. Lag times were obtained from computer-generated growth curves. The 24 hour inhibitory concentration ($IC_{24}$) was defined as the average antibiotic concentration (N$\geq$3) that produced a culture lag time of 24$\pm$1 h. This data provided parametric parameters for statistical measurement (i.e., Student's t test). Some bacteria were analyzed for susceptibility by agar diffusion on blood or Mueller-Hinton agar plates, with adherence to NCCLS standards. Bactericidal activity (99.9% reduction in CFU/ml) of various mixtures of BisBAL was evaluated in liquid medium using *E. coli* ATCC25922. *H. pylori* susceptibility to BisBAL was tested on blood agar plates in Campy pouch bags (Becton Dickinson, Cockeysville, Md.) on Blood agar. Plates were incubated at 36° C. for 5 days. Susceptibility was also measured by agar dilution.

The culture medium component effects on BisBAL activity were assessed in chemically-defined medium by adding limiting or excessive amounts of each essential ingredient. Oxygen tension effects were determined by agar diffusion in aerobic, microaerophilic (Candle jar), and anaerobic (GasPak) conditions. Filter paper discs were impregnated with 157 $\mu$g $Bi^{3+}$, 186 $\mu$g BAL or 157 $\mu$g/31 $\mu$g BisBAL (3:1 molar ratio). Other amounts and ratios were tested. Culture condition effects, such as pH or temperature were evaluated in broth mediums.

Resistant Bacteria

Aminoglycoside-resistant *Psudomonas aeruginosa* strains were tested, including both enzyme-inactivating and reduced permeability strains. Multiply-resistant (mar or sox) mutants of *E. coli* were tested, since such bacteria use efflux mechanisms to resist antibiotics. Several clinical isolates of Providencia, Serratia and Xanthomonas were examined for BisBAL sensitivity, since these bacteria tend to be resistant to chlorhexidine (CHX). Proteus also tends toward resistance to CHX. *Pseudomonas cepacia* was tested. This is one of the most resistant species.

Results

BisBAL was found to be particularly effective against gram-positive organisms such as methicillin-resistant *Staphylococcus aureus* (MRSA). Even vancomycin-resistant enterococci (VRE) were inhibited by BisBAL. Zone diameters of inhibition produced by agents against both antibiotic-resistant species after 24 h incubation at 37° C. are summarized in Table II.

TABLE II

Susceptibility of resistant Gram-positive bacteria to BisBAL

| Bacterial Strain (# of isolates) | $Bi(NO_3)_3$ (157 $\mu$g) | BAL (186 $\mu$g) | BisBAL (157/31 $\mu$g) |
|---|---|---|---|
| MRSA (27) | 7.3 ± 2.8 | $\leq$6.0 | 18.6 ± 3.5 |
| VRE (10) | 7.3 ± 1.4 | $\leq$6.0 | 9.7 ± 0.8 |

Zones of Inhibition (mm) for:

All strains of VRE and MRSA tested were inhibited by BisBAL, but were minimally inhibited by $Bi(NO_3)_3$ and not inhibited by BAL alone. MRSA were particularly sensitive, showing a further partial zone of inhibition of 27.9±2.5 mm. No partial zones were seen with VRE isolates.

In broth dilution studies, the staphylococci are most sensitive to BisBAL, with MIC (minimal inhibitory concentration) values for *S. aureus* typically around 1/0.33 $\mu$M, compared to 15/5 $\mu$M for VRE. Thus BisBAL may be useful against multiply resistant gram-positive bacteria of medical importance. In addition, BisBAL may help eradicate gram positive organisms colonizing for example, the nose, the skin, sinuses or the digestive tract.

Gram-negative bacteria were also found to be quite sensitive to BisBAL. All of the gut pathogens were uniformly sensitive. Using the 24 hour inhibitory concentration ($IC_{24}$) as the endpoint, the following bacteria were grown in Mueller-Hinton II overnight: *Vibrio cholerae, Salmonella typhimurium, Shigella flexneri, Yersinia enterocolitica,* enterotoxigenic and enteroinvasive *E. coli*. *E. coli* and Salmonella grew well in the presence of 250–500 $\mu$M $Bi^{3+}$, while *V.cholerae, S.flexneri,* and *Y.enterocolitica* could withstand up to 50 $\mu$M $Bi^{3+}$. Neither the culture lag time nor the final culture turbidity at 18 hour was affected more than marginally by these $Bi^{3+}$ concentrations. In stark contrast, Bi3+ at 12 $\mu$M (4.3 $\mu$g/ml) combined with 3 $\mu$M BAL(0.37 $\mu$g/ml) was completely inhibitory to all bacteria. Bacteriostatic and bactericidal concentrations for *E.coli* ATCC 25922 were similar (approx. 15 $\mu$M $Bi^{3+}$/5 $\mu$M BAL). Multiply-resistant (mar or sox) mutants of *E.coli* were also equally sensitive to BisBAL. Other gram-negative aerobic bacilli, such as *K. pneumoniae* ($IC_{24}$=30/10 $\mu$M) and *Pseudomonas aeroginosa* ($IC_{24}$=8/2.7 $\mu$M) also showed sensitivity to BisBAL. Of the 10 *P. aeruginosa* strains resistant to aminoglycoside antibiotics, all were equally sensitive to BisBAL, regardless of whether they were aminoglycoside permeability or enzyme-inactivating mutants. Six strains of Proteus, two of Providencia and one Serratia strain also showed low sensitivity ($\leq$30/10 $\mu$M). Seven Xanthomonas isolates were similarly sensitive. Seven strains of *V. cholerae* including ogawa and Inaba, were all sensitive below 15/5 $\mu$M BisBAL. A single clinical isolate of *Pseudomonas cepacia* was the only strain showing higher MICs (90/30 $\mu$M).

Anaerobes were also tested, with *Actimomyces odontolyticus* being inhibited at 22.5/45 $\mu$M, Clostridium spp. at 50/100 $\mu$M, and Bacteriodes spp. at 100/200 $\mu$M BisBAL. *Helicobacter pylori* shows sensitivity to BisBAL at 20/40 $\mu$M.

As the data clearly shows, all of the gram-positive and gram-negative bacteria and anaerobic and aerobic bacteria tested were sensitive to BisBAL. It should be noted that the greater resistance against BisBAL which was found among Bacteriodes may be useful, since they are considered normal flora in the gut. In addition, BisBAL has been found to be particularly active against both staphylococci and *P. aeruginosa*, which is an unusual and very useful characteristic for an antibacterial agent.

Since bacteria inhabiting the gastrointestinal tract thrive under anaerobic conditions, the inhibitory potency of BisBAL in an anaerobic environment was determined. Six *E.coli* were tested by agar diffusion, using a BBL GasPak-Plus Anaerobic system (Becton Dickinson, Cockeysville, Md.). The strains chosen were those which had been used in iron uptake studies, since bismuth antibacterial activity can be reversed by iron. The results are summarized in Table III.

TABLE III

Influence of Anaerobic Conditions on Bi/BAL Sensitivity

| Bacteria | Zone diameter (mm) for BisBAL: | |
| --- | --- | --- |
|  | +$O_2$ | -$O_2$ |
| *E.coli* AB1515-1 (wt) | 12.6 | 11.0 |
| *E.coli* AB1515-1F ($Fe^{2+}$) | 15.0 | 11.8 |
| *E.coli* H1443 (wt) | 11.8 | 10.0 |
| *E.coli* H854 (fiu) | 11.4 | 10.0 |
| *E.coli* C1087 (cir) | 11.9 | 11.4 |
| *E.coli* C1072 (tonB) | 12.2 | 10.4 |

The data show that there was only a 10–20% decrease in BisBAL activity under anaerobic conditions. Agar diffusion studies employing strict anaerobes *Clostridium perfringens* and *Bacteriodes fragilis* also suggest that BisBAL is minimally affected in the absence of $O_2$ possibly due to reduced solubility. Ten clinical isolates of *Helicobacter pylori* have also been tested in a microaerophilic atmosphere for sensitivity to BisBAL by agar diffusion. While $Bi^{3+}$ (157 $\mu$g) or BAL (186 $\mu$g) alone produced little or no zones of inhibition, BisBAL (157/31 $\mu$g) typically produced zone diameters between 8 and 10 mm.

BisBAL is a powerful antimicrobial agent. In comparison to either $Bi^{3+}$ or BAL alone, BisBAL activity is orders of magnitude more potent. With few exceptions, other bismuth compounds or BAL show MICs in the range of 1–10 mM, and are 100 to 1000-fold less potent than BisBAL. Other trivalent metals (e.g., $Sb^{3+}$, $Al^{3+}$, $Ga^{3+}$, $Cr^{3+}$, $Ru^{3+}$, $Fe^{3+}$, $Sc^{3+}$, $y^{3+}$) when chelated with BAL do not exhibit enhanced antibacterial activity.

It has also been shown that, in contrast to $Bi^{3+}$, the antibacterial effects of BisBAL are independent of the iron concentration. The antibacterial effects of $Bi^{3+}$ (or other trivalent metals) can be reversed by addition of micromolar amounts of iron to culture medium. However, even millimolar amounts of iron do not reverse or diminish the effects of BisBAL on bacteria. The lack of dependence of the BisBAL composition on iron concentration, as opposed to other bismuth compounds, is of therapeutic benefit in the lower GI tract where the conditions are anaerobic and iron is ample. BisBAL has been shown to have considerable effects on gut flora, while BSS alone does not have a significant growth-inhibiting effect on these bacteria. In particular, a single BisBAL dose reduced the production of fecal material by 60% in rats over a 24 hour period.

It has also been found that other cations, e.g., copper, silver and gold, do have a neutralizing effect on BisBAL activity. In particular, copper at 78 $\mu$M neutralized the inhibitory effects of 1x and 10x, but not 100x the MIC of BisBAL. Therefore, these antagonists could be used to neutralize BisBAL when necessary.

BisBAL is also able to markedly inhibit capsular polysaccharide (CPS) production. CPS is produced by many bacteria for protection against dessication and for camouflage against host defenses. As shown in FIG. 1, experiments were performed which showed that at 0.25 of the MIC for *Klebsiella pneumoniae*, BisBAL was able to inhibit 60% of the capsule expression and at less than one half of the MIC, BisBAL reduced the capsule expression by more than 80%, as determined by a chemical assay for sugars. In contrast, chlorhexidine (CHX), a topical agent useful as an antiseptic, a disinfectant and a preservative, had no significant effect on CPS expression even at 0.75 of the MIC. This reduction in capsule expression is important, since as the CPS surface coating is reduced, the bacteria become increasingly vulnerable to phagocytic uptake by white blood cells (WBC) in the presence of anti-capsular antiserum. It was also shown that at less than 0.5 of the MIC, the number of bacteria phagocytosed per 100 WBC increased from 19 without BisBAL treatment to more than 600 with BisBAL treatment. Although some other bismuth compounds have a similar effect on CPS expression and phagocytic uptake, a 100-fold higher concentration is required. Moreover, as discussed above, the addition of iron to culture media neutralizes the anti-CPS effect of $Bi(NO_3)_3$ or BSS, but does not effect that of BisBAL.

BisBAL was also shown to effectively inhibit biofilm organisms. In particular, BisBAL was shown to be as effective against bacteria in biofilms as it is on planktonic bacteria. No other known medication has this capacity.

BisBAL has strong adherence properties which should increase the safety and tolerance of the composition since BisBAL attaches firmly to tissue upon initial contact instead of flowing freely through the blood. In addition, these properties of BisBAL add to the bacterial persistence of the composition since the composition adheres tightly to the skin, the gut mucosa and other tissues, thereby providing protection for increased periods of time.

It should be understood that the BisBAL composition can be combined with other agents that improve its overall value or usefulness. In particular, additives, such as antioxidants, can be used with BisBAL to prolong shelf-life. Antioxidants such as tocopheral have been shown to be compatible with BisBAL. In addition, polycationic detergents, such as cetrimide or Zwittergent 3-14, could be added as these have been shown to improve the activity of the composition. BisBAL is 100-fold more resistant to neutralization by detergents (e.g., SDS, Tween 80) than is CHX, another membrane-active biocide. Therefore, it is easier to combine BisBAL with soaps and detergents. Furthermore, antibiotic mixtures, antifungal, antimycobacterial or antiviral agents which increase coverage or potency can be included, particularly those against H. pylori which are useful against ulcerative diseases of the GI tract. Finally, other compounds, such as alkali, buffering agents, $H_2$-blockers, or the like that increase pH in situ and improve solubility and carrier compounds miscible with BisBAL that change consistency or persistence can be included. It is also contemplated that since BAL has a disagreeable odor, other agents can be added to improve the taste or smell of the resulting product.

BisBAL is useful for inhibiting and preventing infection by a wide variety of infectious agents and pathogens. The composition can be provided orally, intraperitoneally, intramuscularly, subdermally, intravenously, and topically. It can be provided as a liquid, powder, tablet, or a capsule. It is also contemplated that the composition can be used to coat medical devices or implants, such as catheters, or concentrated in surgical scrubs. BisBAL can also be incorporated into soaps as an antibacterial agent, or used in deodorant/antiperspirants (feet or underarm use), mouthwashes, contact lens solution, cleaners, paints, food, and other perishable products. Moreover, BisBAL can be used to inhibit biofilm formation on industrial equipment, such as in pulp and paper manufacturing, in water towers, ventilators, air-conditioners, or incorporated in an antifouling mixture. BisBAL is useful for preventing or killing biofilm populations on various devices, in swimming pools, boats, and other surfaces subjected to humid conditions. Finally, it could also be employed as a preservative or antiseptic in cosmetics or personal care products.

Although the mechanisms of action of BisBAL are not fully understood, it is known that the activity of BisBAL can not be accounted for by increased solubility alone, since the highly soluble form ($Bi^{3+}$/BAL ratio=1:2) is not the most active moiety. Instead, a 100-fold less soluble species (ratio= 3:1) is the most active form. In addition, other thiol-containing chelators, namely dimercapto-succinic acid (DMSA), 2,3-dimercaptopropane-1-sulfonic acid (DMPS), and the amino acid cysteine, also solubilize bismuth as well or better than BAL, but they do not increase its antibacterial properties.

BisBAL has been characterized as amphipathic (amphiphilic) as well as polycationic. Compounds with such properties are typically membrane-active agents; i.e., they act primarily by disrupting bacterial membranes. Electron micrographs of E. coli treated with 100/33.3 $\mu$M BisBAL support these findings. BisBAL does not appear to enter the cell, but rather produces vacuoles, perhaps due to cytoplasmic leakage. An increase in extracellular pentose shortly after BisBAL treatment of E. coli also suggests the release of nucleic acid.

It is also thought that BisBAL may exert its effects by inactivating membrane enzymatic activity, particularly that of membrane ATPase, by thiol exchange of $Bi^{3+}$. Capsule and slime expression is energy-intensive, and is virtually shut off by BisBAL at subinhibitory levels; likely a result of ATPase inhibition. Being nonessential, CPS production can be turned off before bacterial growth is affected. Such inhibition occurs at greater than 500 $\mu$M for $Bi(NO_3)_3$, but at 5 $\mu$M for BisBAL. As discussed above, the marked increase in potency can not be explained by the increased solubility in water. It is instead thought the novel structure of BisBAL promotes permeation into bacterial membranes. Penetration through the outer membrane of gram-negative bacteria appears to be largely independent of porins and is not influenced by antibiotic efflux mechanisms. Rather, BisBAL penetrates the outer membrane similarly to CHX or polymyxin B; its polycationic amphiphilic structure promotes an attraction to the negatively-charged, amphiphilic outer membrane.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A composition, comprising:
   a trivalent bismuth salt; and
   at least one compound selected from the group consisting of dimercaprol, β-mercaptoethanol and dithiothreitol, wherein the molar ratio of said trivalent bismuth salt to said compound is approximately 1:2 to approximately 3:1.

2. A composition, as recited in claim 1, wherein said trivalent bismuth salt is selected from the group consisting of bismuth nitrate, colloidal bismuth subcitrate and bismuth subsalicylate.

3. A composition, as recited in claim 1, wherein said molar ratio is approximately 1:1 to approximately 3:1.

4. A composition, as recited in claim 1, wherein said molar ratio is approximately 2:1 to approximately 3:1.

5. A composition, as recited in claim 1, further comprising a pharmaceutically acceptable diluent or carrier.

6. A composition, comprising:
   a trivalent bismuth salt; and
   at least one compound selected from the group consisting of dimercaprol, β-mercaptoethanol and dithiothreitol, wherein said trivalent bismuth salt and said compound are present in the molar ratio of approximately 3:1.

7. A method of preventing or inhibiting bacterial infection, comprising the step of:
   administering a therapeutically effective amount of a composition comprising a trivalent bismuth salt and at least one compound selected from the group consisting of dimercaprol, β-mercaptoethanol and dithiothreitol to a patient, in need thereof.

8. A method, as recited in claim 7, wherein said trivalent bismuth salt is selected from the group consisting of bismuth nitrate, colloidal bismuth subcitrate and bismuth subsalicylate.

9. A method, as recited in claim 8, wherein the molar ratio of said trivalent bismuth salt to said compound is not less than approximately 1:2 nor more than approximately 3:1.

10. A method, as recited in claim 9, wherein said molar ratio is approximately 1:1 to approximately 3:1.

11. A method, as recited in claim 9, wherein said molar ratio is approximately 2:1 to approximately 3:1.

12. A method of eradicating bacteria, comprising the step of:
   applying to an area on which it is desired to eradicate bacteria an effective amount of a composition comprising a trivalent bismuth salt and at least one compound selected from the group consisting of dimercaprol, β-mercaptoethanol and dithiothreitol.

13. A method, as recited in claim 12, wherein said trivalent bismuth salt is selected from the group consisting of bismuth nitrate, colloidal bismuth subcitrate and bismuth subsalicylate.

14. A method, as recited in claim 13, wherein the molar ratio of said trivalent bismuth salt to said compound is not less than approximately 1:2 nor more than approximately 3:1.

15. A method, as recited in claim 14, wherein said molar ratio is approximately 1:1 to approximately 3:1.

16. A method, as recited in claim 14, wherein said molar ratio is approximately 2:1 to approximately 3:1.

17. A method of preventing the formation or growth of biofilms, comprising the step of:

applying to an area on which it is desired to prevent the formation or growth of biofilms an effective amount of a composition comprising a trivalent bismuth salt and at least one compound selected from the group consisting of dimercaprol, $\beta$-mercaptoethanol and dithiothreitol.

18. A method of preventing spoilage, comprising the step of:

applying to a product on which it is desired to prevent spoilage an effective amount of a composition comprising a trivalent bismuth salt and at least one compound selected from the group consisting of dimercaprol, $\beta$-mercaptoethanol and dithiothreitol.

* * * * *